US012600706B2

(12) United States Patent
Liao et al.

(10) Patent No.: US 12,600,706 B2
(45) Date of Patent: *Apr. 14, 2026

(54) METHOD FOR MANUFACTURING LOW-VISCOSITY HARDENER

(71) Applicant: NAN YA PLASTICS CORPORATION, Taipei (TW)

(72) Inventors: Te-Chao Liao, Taipei (TW); Jung-Jen Chuang, Taipei (TW); Chung-Yu Chen, Taipei (TW); Jung-Tsu Wu, Taipei (TW)

(73) Assignee: NAN YA PLASTICS CORPORATION, Taipei (TW)

( * ) Notice: Subject to any disclaimer, the term of this patent is extended or adjusted under 35 U.S.C. 154(b) by 627 days.

This patent is subject to a terminal disclaimer.

(21) Appl. No.: 18/152,968

(22) Filed: Jan. 11, 2023

(65) Prior Publication Data

US 2024/0140925 A1 May 2, 2024

(30) Foreign Application Priority Data

Oct. 28, 2022 (TW) ................................. 111140987

(51) Int. Cl.
| | |
|---|---|
| *C07D 307/77* | (2006.01) |
| *B01J 23/04* | (2006.01) |
| *B01J 27/24* | (2006.01) |
| *C07D 307/89* | (2006.01) |
| *C08K 5/1539* | (2006.01) |

(52) U.S. Cl.
CPC ............ *C07D 307/77* (2013.01); *B01J 23/04* (2013.01); *B01J 27/24* (2013.01); *C08K 5/1539* (2013.01); *C08K 2201/009* (2013.01)

(58) Field of Classification Search
CPC ............................ C07D 307/77; C07D 307/89
See application file for complete search history.

(56) References Cited

U.S. PATENT DOCUMENTS 12,116,340 B2 * 10/2024 Liao ........................ C07C 51/56

FOREIGN PATENT DOCUMENTS

| | | | |
|---|---|---|---|
| CN | 109824639 | A | 5/2019 |
| CN | 209138602 | U | 7/2019 |
| JP | 54151941 | A | 11/1979 |
| JP | 5589277 | A | 7/1980 |
| JP | 57206678 | A | 12/1982 |
| JP | 1123818 | A | 5/1989 |
| JP | 2002155070 | A | 5/2002 |
| JP | 4774591 | B2 * | 9/2011 |
| JP | 7422850 | B1 | 1/2024 |

* cited by examiner

*Primary Examiner* — Matthew P Coughlin

(74) *Attorney, Agent, or Firm* — Li & Cai Intellectual Property (USA) Office

(57) ABSTRACT

A method for manufacturing a low-viscosity hardener is provided. The method includes the followings steps: providing a hardener crude product; and subjecting the hardener crude product and an alkaline catalyst to an isomerization reaction, so as to obtain the low-viscosity hardener. The hardener crude product contains 3-methyltetrahydrophthalic anhydride and 4-methyltetrahydrophthalic anhydride, and a weight ratio of the 3-methyltetrahydrophthalic anhydride to the 4-methyltetrahydrophthalic anhydride ranges from 7:3 to 3:7. A viscosity of the low-viscosity hardener ranges from 30 cps to 50 cps.

8 Claims, 2 Drawing Sheets

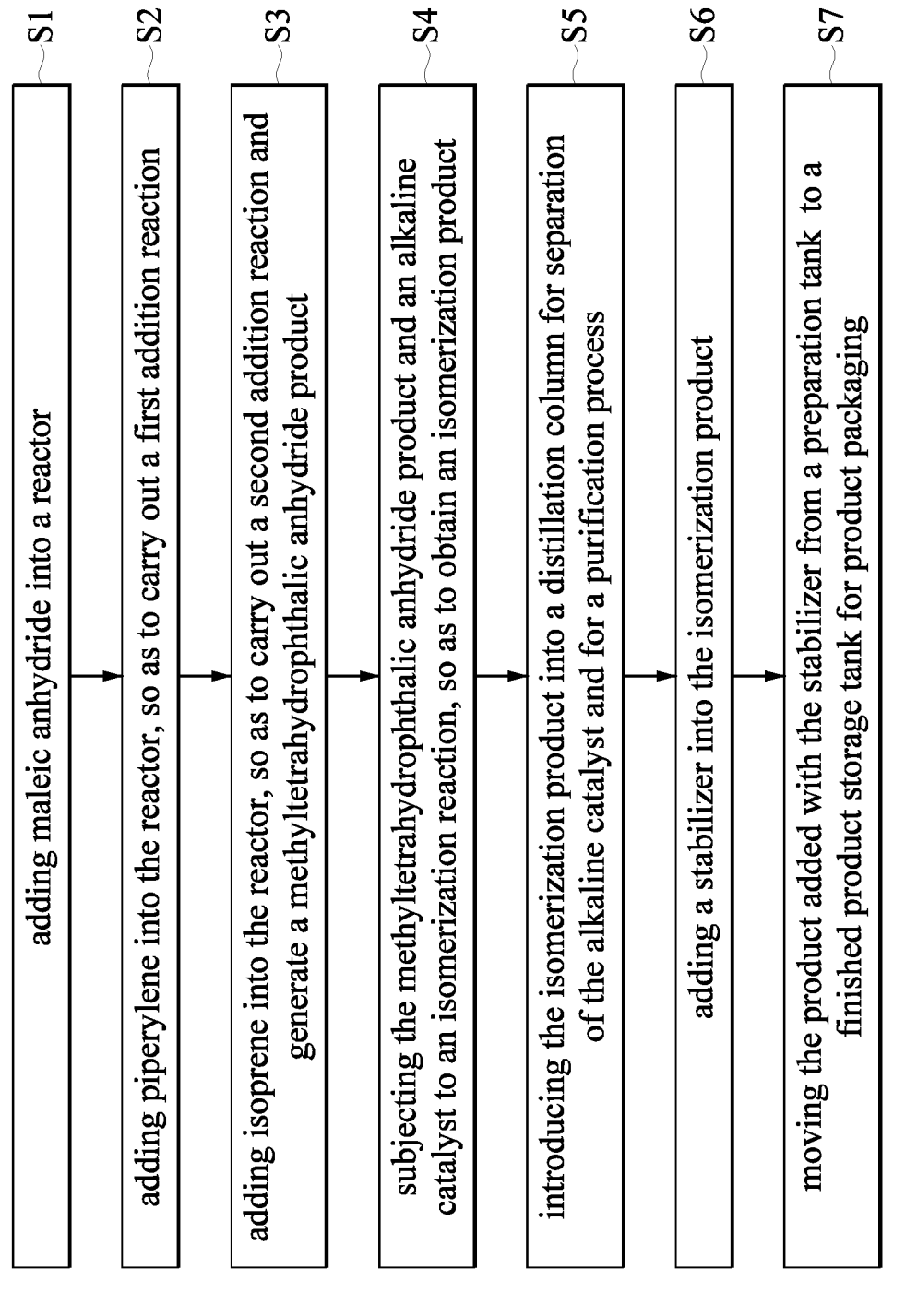

S1 adding maleic anhydride into a reactor

S2 adding piperylene into the reactor, so as to carry out a first addition reaction S3 adding isoprene into the reactor, so as to carry out a second addition reaction and generate a methyltetrahydrophthalic anhydride product S4 subjecting the methyltetrahydrophthalic anhydride product and an alkaline catalyst to an isomerization reaction, so as to obtain an isomerization product S5 introducing the isomerization product into a distillation column for separation of the alkaline catalyst and for a purification process S6 adding a stabilizer into the isomerization product S7 moving the product added with the stabilizer from a preparation tank to a finished product storage tank for product packaging

FIG. 1

METHOD FOR MANUFACTURING LOW-VISCOSITY HARDENER

CROSS-REFERENCE TO RELATED PATENT APPLICATION

This application claims the benefit of priority to Taiwan Patent Application No. 111140987, filed on Oct. 28, 2022. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a method for manufacturing a hardener, and more particularly to a method for manufacturing a low-viscosity hardener.

BACKGROUND OF THE DISCLOSURE

Methyltetrahydrophthalic anhydride is a hardener commonly used in organic acid anhydride epoxy resins. The methyltetrahydrophthalic anhydride has good heat resistance and stability, while still maintaining good physical and electrical properties even in a high temperature environment.

Generally speaking, reactants for synthesizing the methyltetrahydrophthalic anhydride include piperylene, isoprene, and acid anhydride. A conventional method for manufacturing the methyltetrahydrophthalic anhydride is to add the metered reactants into a reactor at a same time, so that the reactants undergo the Diels-Alder reaction (also referred to as a conjugated diene addition reaction). Accordingly, the methyltetrahydrophthalic anhydride can be generated. Then, the methyltetrahydrophthalic anhydride and an acid catalyst (e.g., sulfuric acid and p-toluenesulfonic acid) undergo an isomerization reaction, so as to enhance properties of the methyltetrahydrophthalic anhydride.

However, the methyltetrahydrophthalic anhydride manufactured by the conventional method has a high viscosity, thereby causing processing difficulties. Therefore, how to reduce the viscosity of the methyltetrahydrophthalic anhydride through improvements to steps for processing the same, so as to enhance the processability of the methyltetrahydrophthalic anhydride, has become one of the important issues to be addressed in this industry.

SUMMARY OF THE DISCLOSURE

In response to the above-referenced technical inadequacies, the present disclosure provides a method for manufacturing a low-viscosity hardener.

In one aspect, the present disclosure provides a method for manufacturing a low-viscosity hardener. The method includes the following steps: providing a hardener crude product; and subjecting the hardener crude product and an alkaline catalyst to an isomerization reaction, so as to obtain the low-viscosity hardener. The hardener crude product contains 3-methyltetrahydrophthalic anhydride and 4-methyltetrahydrophthalic anhydride, and a weight ratio of the 3-methyltetrahydrophthalic anhydride to the 4-methyltetrahydrophthalic anhydride ranges from 7:3 to 3:7. A viscosity of the low-viscosity hardener ranges from 30 cps to 50 cps.

In certain embodiments, the isomerization reaction is carried out at a temperature ranging from 130° C. to 160° C.

In certain embodiments, the alkaline catalyst is selected from the group consisting of potassium carbonate, sodium carbonate, sodium hydroxide, potassium hydroxide, ethanolamine, diethanolamine, and triethanolamine.

In certain embodiments, a content ratio of trans-3-methyltetrahydrophthalic anhydride to cis-3-methyltetrahydrophthalic anhydride in the low-viscosity hardener ranges from 1.1:1 to 4.8:1.

In certain embodiments, a content ratio of trans-3-methyltetrahydrophthalic anhydride to cis-3-methyltetrahydrophthalic anhydride in the hardener crude product ranges from 1:4 to 1:7.

In certain embodiments, the method further includes: feeding maleic anhydride into a reactor; adding piperylene into the reactor, so that the piperylene and the maleic anhydride undergo a first addition reaction; and adding isoprene into the reactor, so that the isoprene and the maleic anhydride undergo a second addition reaction to obtain the hardener crude product.

In certain embodiments, when a conversion rate of the maleic anhydride is greater than 25%, the first addition reaction is complete and the isoprene is added into the reactor.

In certain embodiments, the first addition reaction is carried out at a temperature ranging from 80° C. to 120° C., and the second addition reaction is carried out at a temperature ranging from 80° C. to 120° C.

In certain embodiments, when a content of the maleic anhydride is less than 100 ppm, the second addition reaction is complete.

In certain embodiments, a purity of the piperylene ranges from 65% to 75%, and a purity of the isoprene is greater than 99%.

Therefore, in the method for manufacturing the low-viscosity hardener provided by the present disclosure, by virtue of "controlling contents of the 3-methyltetrahydrophthalic anhydride and the 4-methyltetrahydrophthalic anhydride in the hardener crude product" and "adding the alkaline catalyst for the isomerization reaction," an effect of reducing the viscosity of the hardener can be achieved. In this way, the low-viscosity hardener can have a wider applicability.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which:

FIG. 1 is a flowchart of a method for manufacturing a low-viscosity hardener according to the present disclosure.

DETAILED DESCRIPTION OF THE EXEMPLARY EMBODIMENTS

Figure 2:
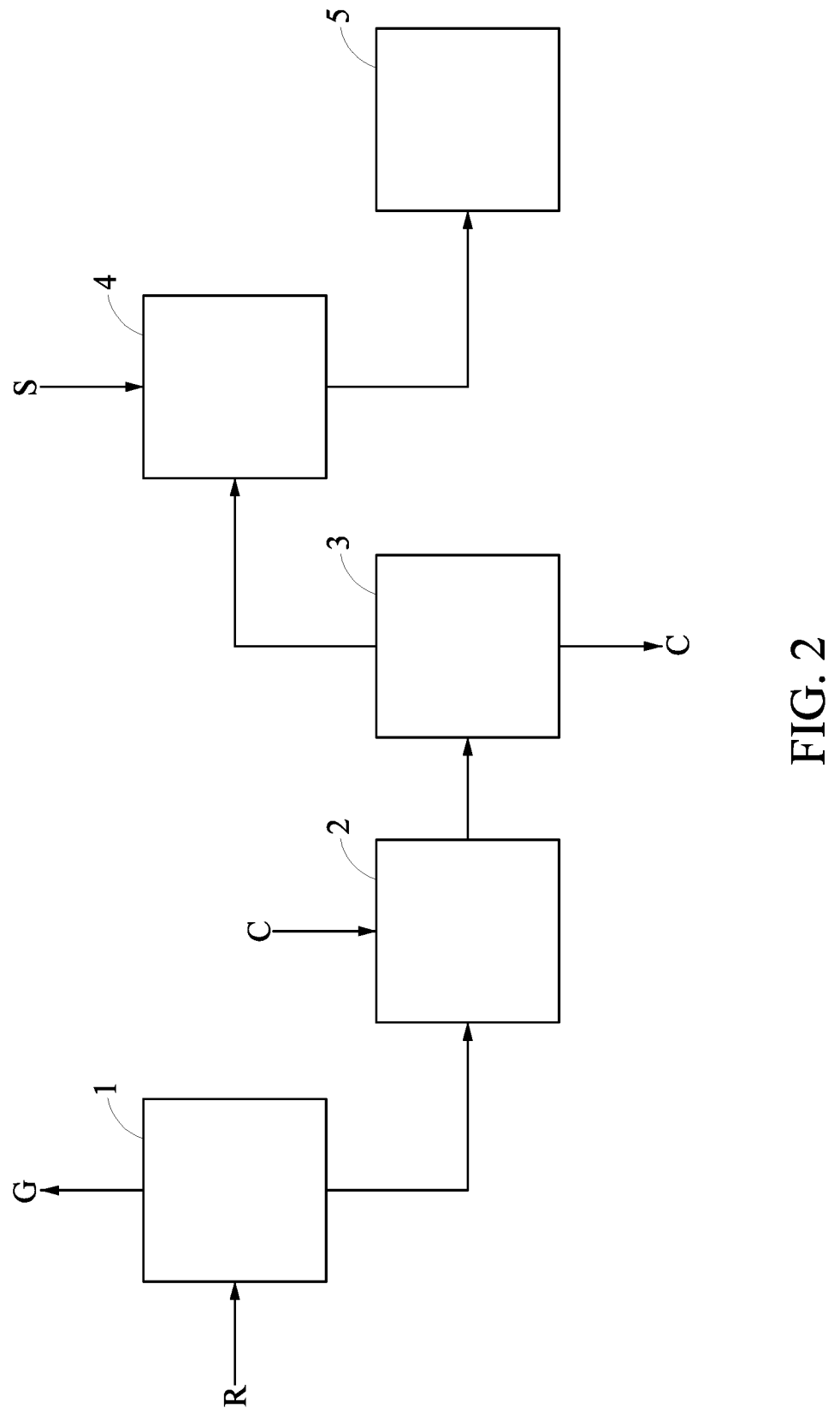
FIG. 2 is a schematic view showing apparatuses for manufacturing the low-viscosity hardener according to the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Different from a conventional method for manufacturing a hardener, components (3-methyltetrahydrophthalic anhydride and 4-methyltetrahydrophthalic anhydride) of a hardener crude product and contents thereof are controlled in the present disclosure. Further, an alkaline catalyst is added for an isomerization reaction, so as to achieve an effect of reducing a viscosity of the hardener. In this way, a low-viscosity hardener of the present disclosure can have a good processability and a wider applicability.

In the present disclosure, the hardener crude product that contains methyltetrahydrophthalic anhydride is first provided. Specifically, the hardener crude product contains the 3-methyltetrahydrophthalic anhydride and the 4-methyltetrahydrophthalic anhydride. To be specific, a weight ratio of the 3-methyltetrahydrophthalic anhydride to the 4-methyltetrahydrophthalic anhydride ranges from 7:3 to 3:7. For example, a content ratio of the 3-methyltetrahydrophthalic anhydride to the 4-methyltetrahydrophthalic anhydride can be 6:4, 5:5, or 4:6. Preferably, the content of the 3-methyltetrahydrophthalic anhydride is greater than or equal to the content of the 4-methyltetrahydrophthalic anhydride.

A melting point of the 3-methyltetrahydrophthalic anhydride is lower than a melting point of the 4-methyltetrahydrophthalic anhydride. When the content of the 3-methyltetrahydrophthalic anhydride in the hardener crude product is low, the hardener crude product can have a higher viscosity. When the content of the 3-methyltetrahydrophthalic anhydride in the hardener crude product is high, the hardener crude product can have a lower viscosity. As such, in the present disclosure, the viscosity of the hardener can be adjusted by controlling the weight ratio of the 3-methyltetrahydrophthalic anhydride to the 4-methyltetrahydrophthalic anhydride.

Then, the hardener crude product and the alkaline catalyst are subjected to the isomerization reaction at a temperature ranging from 130° C. to 160° C., so as to obtain the low-viscosity hardener. To be specific, in the isomerization reaction, it is the 3-methyltetrahydrophthalic anhydride in the hardener crude product that is isomerized. In this way, cis-3-methyltetrahydrophthalic anhydride is reconstituted into trans-3-methyltetrahydrophthalic anhydride for adjusting a content ratio of the trans-3-methyltetrahydrophthalic anhydride to the cis-3-methyltetrahydrophthalic anhydride.

Before the isomerization reaction, a content of the trans-3-methyltetrahydrophthalic anhydride is lower than a content of the cis-3-methyltetrahydrophthalic anhydride in the hardener crude product. After the isomerization reaction, the content of the trans-3-methyltetrahydrophthalic anhydride is greater than the content of the cis-3-methyltetrahydrophthalic anhydride in the low-viscosity hardener. In the low-viscosity hardener, the content ratio of the trans-3-methyltetrahydrophthalic anhydride to the cis-3-methyltetrahydrophthalic anhydride can be monitored by a gas chromatograph (brand: Agilent; brand: 8860 GC). In one exemplary embodiment, the content ratio of the trans-3-methyltetrahydrophthalic anhydride to the cis-3-methyltetrahydrophthalic anhydride ranges from 1.1:1 to 4.8:1 (e.g., 1.5:1, 2:1, 2.5:1, 3:1, 3.5:1, 4:1, or 4.5:1).

After the content of the trans-3-methyltetrahydrophthalic anhydride in the low-viscosity hardener is increased, the viscosity of the low-viscosity hardener can be decreased, thereby allowing a final product to have a wider applicability. To be specific, the viscosity of the low-viscosity hardener can range from 30 cps to 50 cps (e.g., 35 cps, 40 cps, or 45 cps).

The alkaline catalyst used in the isomerization reaction can be an organic base or an inorganic base. The organic base can be alcoholamines (especially one selected from the group consisting of ethanolamine, diethanolamine, and triethanolamine), and the inorganic base can be selected from the group consisting of potassium carbonate, sodium carbonate, sodium hydroxide, and potassium hydroxide.

With regard to the method for manufacturing the hardener of the present disclosure, Examples 1 to 4 below are exemplarily provided for convenience of description. Reaction parameters of Examples 1 to 4 are shown in Table 1.

Example 1

The hardener crude product (having a total weight of 10,000 kilograms) is fed into an isomerization tank, and the hardener crude product contains 7,000 kilograms of the 3-methyltetrahydrophthalic anhydride (the content ratio of the trans-3-methyltetrahydrophthalic anhydride to the cis-3-methyltetrahydrophthalic anhydride being 1:5.6) and 3,000 kilograms of the 4-methyltetrahydrophthalic anhydride.

After 60 kilograms of the sodium hydroxide (the alkaline catalyst) is added, the isomerization reaction proceeds at a temperature of 140° C. for 24 hours, so as to obtain the low-viscosity hardener. Based on a detection made by the gas chromatograph, the content ratio of the trans-3-methyltetrahydrophthalic anhydride to the cis-3-methyltetrahydrophthalic anhydride in the low-viscosity hardener is 4.03:1, and the viscosity of the low-viscosity hardener is 34 cps.

Example 2

The hardener crude product (having a total weight of 10,000 kilograms) is fed into the isomerization tank, and the hardener crude product contains 7,000 kilograms of the 3-methyltetrahydrophthalic anhydride (the content ratio of the trans-3-methyltetrahydrophthalic anhydride to the cis-3-methyltetrahydrophthalic anhydride being 1:5.6) and 3,000 kilograms of the 4-methyltetrahydrophthalic anhydride.

After 60 kilograms of the diethanolamine (the alkaline catalyst) is added, the isomerization reaction proceeds at a temperature of 140° C. for 24 hours, so as to obtain the low-viscosity hardener. Based on the detection made by the gas chromatograph, the content ratio of the trans-3-methyl-tetrahydrophthalic anhydride to the cis-3-methyltetrahymethyltetrahydrophthalic anhydride being 1:5.6) and 3,000 kilograms of the 4-methyltetrahydrophthalic anhydride.

After 60 kilograms of the triethanolamine (the alkaline catalyst) is added, the isomerization reaction proceeds at a temperature of 140° C. for 24 hours, so as to obtain the low-viscosity hardener. Based on the detection made by the gas chromatograph, the content ratio of the trans-3-methyl-tetrahydrophthalic anhydride to the cis-3-methyltetrahy-drophthalic anhydride in the low-viscosity hardener is 3.75:1, and the viscosity of the low-viscosity hardener is 36 cps.

TABLE 1

|  | Example 1 | Example 2 | Example 3 | Example 4 |
|---|---|---|---|---|
| Weight ratio of 3-methyltetrahydrophthalic anhydride to 4-methyltetrahydrophthalic anhydride in hardener crude product | 7:3 | 7:3 | 7:3 | 7:3 |
| Content ratio of trans-3-methyltetrahydrophthalic anhydride to cis-3-methyltetrahydrophthalic anhydride in hardener crude product | 1:5.6 | 1:5.6 | 1:5.6 | 1:5.6 |
| Alkaline catalyst | Sodium hydroxide | Diethanolamine | Sodium hydroxide | Triethanolamine |
| Isomerization reaction temperature | 140° C. | 140° C. | 150° C. | 140° C. |
| Isomerization reaction time | 24 hours | 24 hours | 24 hours | 24 hours |
| Content ratio of trans-3-methyltetrahydrophthalic anhydride to cis-3-methyltetrahydrophthalic anhydride in low-viscosity hardener | 4.03:1 | 3.64:1 | 4.31:1 | 3.75:1 |
| Viscosity of low-viscosity hardener | 34 cps | 37 cps | 33 cps | 36 cps | drophthalic anhydride in the low-viscosity hardener is 3.64:1, and the viscosity of the low-viscosity hardener is 37 cps.

Example 3

The hardener crude product (having a total weight of 10,000 kilograms) is fed into the isomerization tank, and the hardener crude product contains 7,000 kilograms of the 3-methyltetrahydrophthalic anhydride (the content ratio of the trans-3-methyltetrahydrophthalic anhydride to the cis-3-methyltetrahydrophthalic anhydride being 1:5.6) and 3,000 kilograms of the 4-methyltetrahydrophthalic anhydride.

After 60 kilograms of the sodium hydroxide (the alkaline catalyst) is added, the isomerization reaction proceeds at a temperature of 150° C. for 24 hours, so as to obtain the low-viscosity hardener. Based on the detection made by the gas chromatograph, the content ratio of the trans-3-methyl-tetrahydrophthalic anhydride to the cis-3-methyltetrahy-drophthalic anhydride in the low-viscosity hardener is 4.31:1, and the viscosity of the low-viscosity hardener is 33 cps.

Example 4

The hardener crude product (having a total weight of 10,000 kilograms) is fed into the isomerization tank, and the hardener crude product contains 7,000 kilograms of the 3-methyltetrahydrophthalic anhydride (the content ratio of the trans-3-methyltetrahydrophthalic anhydride to the cis-3-

From the content of Examples 1 to 4, it can be observed that the effect of reducing the viscosity of the hardener can be achieved by controlling the components of the hardener crude product and the contents thereof and by partially reconstituting the cis-3-methyltetrahydrophthalic anhydride into the trans-3-methyltetrahydrophthalic anhydride with use of the alkaline catalyst. Specifically, the viscosity of the low-viscosity hardener ranges from 32 cps to 38 cps. Further, it can be found from a comparison of catalytic effects of different alkaline catalysts that the inorganic base has a better reaction effect than the organic base.

As mentioned above, the weight ratio of the 3-methyltet-rahydrophthalic anhydride to the 4-methyltetrahydroph-thalic anhydride can affect the viscosity of the hardener. Therefore, the method of the present disclosure further includes a step of synthesizing the methyltetrahydrophthalic anhydride (the hardener crude product) from piperylene, isoprene, and maleic anhydride.

Reference is made to FIG. 1 and FIG. 2, in which FIG. 1 is a flowchart of a method for manufacturing a low-viscosity hardener according to the present disclosure, and FIG. 2 shows apparatuses for manufacturing the low-viscosity hardener. The apparatuses shown in FIG. 2 can be used to implement the method of the present disclosure, but steps in the present disclosure will not be limited thereby.

In steps S1 to S3, reactants R (the maleic anhydride, the piperylene, and the isoprene) are added into a reactor 1. After two addition reactions (i.e., a first addition reaction and a second addition reaction), a methyltetrahydrophthalic anhydride product (the hardener crude product) in a crystalline solid state can be generated. Since an impurity G in the reactant R (especially an impurity in the piperylene) does not react with the maleic anhydride, after the methyltetrahydrophthalic anhydride product is generated, the impurity G can be discharged from the reactor 1 in the form of a gas and be separated from the methyltetrahydrophthalic anhydride product.

In step S1, the maleic anhydride is added into the reactor 1. By heating the reactor 1 to a temperature of from 60° C. to 75° C., the maleic anhydride is in a liquid state (which facilitates the reaction).

In step S2, the piperylene is added into the reactor 1. To be specific, the piperylene is introduced into the reactor 1 in the form of a gas. The reactor 1 is heated to a temperature of from 80° C. to 120° C., so as to carry out the first addition reaction. In the first addition reaction, the maleic anhydride reacts with the piperylene to generate the 3-methyltetrahydrophthalic anhydride.

Due to differences in three-dimensional structure, the 3-methyltetrahydrophthalic anhydride generated in the first addition reaction has an optical isomer. Specifically, the content of the trans-3-methyltetrahydrophthalic anhydride is less than the content of the cis-3-methyltetrahydrophthalic anhydride. In one exemplary embodiment, the content ratio of the trans-3-methyltetrahydrophthalic anhydride to the cis-3-methyltetrahydrophthalic anhydride ranges from 1:4 to 1:7 (e.g., 1:4.5, 1:5, 1:5.5, 1:6, or 1:6.5). If a ratio relationship between the trans-3-methyltetrahydrophthalic anhydride and the cis-3-methyltetrahydrophthalic anhydride is to be further adjusted, the methyltetrahydrophthalic anhydride product (the hardener crude product) needs to undergo the isomerization reaction (step S4). In the following paragraphs, specific steps of the isomerization reaction will be illustrated.

By adjusting the time taken for the first addition reaction, an effect of controlling the content ratio of the 3-methyltetrahydrophthalic anhydride to the 4-methyltetrahydrophthalic anhydride in the methyltetrahydrophthalic anhydride product can be achieved. In the present disclosure, when a conversion rate of the maleic anhydride is greater than 25%, the first addition reaction is complete. That is, in the to-be-generated methyltetrahydrophthalic anhydride of the present disclosure, a content of the 3-methyltetrahydrophthalic anhydride is at least 25 wt %. Specifically, the first addition reaction can optionally be stopped when the conversion rate of the maleic anhydride reaches 30%, 35%, 40%, 45%, 50%, 55%, 60%, 65%, 70%, 75%, or 80%.

In step S3, the isoprene is added into the reactor 1. To be specific, the isoprene is introduced into the reactor 1 in the form of a gas. The reactor 1 is heated to a temperature of from 80° C. to 120° C., so as to carry out the second addition reaction. In the second addition reaction, the maleic anhydride reacts with the isoprene to generate the 4-methyltetrahydrophthalic anhydride. In order to reduce manufacturing costs, when a content of the maleic anhydride is less than 100 ppm, the second addition reaction is complete. However, the present disclosure is not limited thereto.

Through the above-mentioned first addition reaction and second addition reaction (steps S1 to S3), the methyltetrahydrophthalic anhydride product (the hardener crude product) in a crystalline solid state can be obtained. The methyltetrahydrophthalic anhydride product contains the 3-methyltetrahydrophthalic anhydride and the 4-methyltetrahydrophthalic anhydride. In addition, the content ratio of the 3-methyltetrahydrophthalic anhydride to the 4-methyltetrahydrophthalic anhydride can be adjusted through the reaction time of the first addition reaction. In one exemplary embodiment, the content ratio of the 3-methyltetrahydrophthalic anhydride to the 4-methyltetrahydrophthalic anhydride ranges from 7:3 to 3:7. For example, the content ratio of the 3-methyltetrahydrophthalic anhydride to the 4-methyltetrahydrophthalic anhydride can be 6:4, 5:5, or 4:6.

In the present disclosure, the maleic anhydride is an excess reagent, and the piperylene and the isoprene are limiting reagents. During the first addition reaction, the maleic anhydride first reacts with the piperylene, so as to generate the 3-methyltetrahydrophthalic anhydride. During the second addition reaction, the remaining maleic anhydride reacts with the isoprene, so as to generate the 4-methyltetrahydrophthalic anhydride. After the two addition reactions (i.e., the first addition reaction and the second addition reaction), the methyltetrahydrophthalic anhydride product contains the 3-methyltetrahydrophthalic anhydride and the 4-methyltetrahydrophthalic anhydride. In this way, a competitive reaction between the piperylene and the isoprene can be prevented, such that an effect of improving a reaction efficiency of reactants can be achieved.

Through a technical solution of adding the reactants in a stepwise manner, the content ratio of the 3-methyltetrahydrophthalic anhydride to the 4-methyltetrahydrophthalic anhydride in the methyltetrahydrophthalic anhydride product can be easily controlled. In addition, methyltetrahydrophthalic anhydride products with expected properties can be manufactured according to practical requirements.

Further, a purity of the reactant can also affect a reaction rate of the reaction. Since the purity of the piperylene currently available on the market is generally lower than that of the isoprene, the piperylene is added before the isoprene in the present disclosure. In the first addition reaction, the maleic anhydride has not yet reacted and thus has a high concentration, which can be used to overcome a problem of low reaction rate caused by the piperylene having a low purity. In the second addition reaction, the maleic anhydride has reacted with the piperylene to form the 3-methyltetrahydrophthalic anhydride, so that the concentration of the maleic anhydride is low. Therefore, the isoprene that has a high purity can be used to overcome the problem of low reaction rate caused by the maleic anhydride having a low concentration. In the present disclosure, the methyltetrahydrophthalic anhydride is prepared in such a manner that the effect of improving the reaction efficiency can be achieved.

In the embodiments of the present disclosure, the purity of the piperylene is less than 80% (from 65% to 75%), and the purity of the isoprene is greater than 99%. However, the present disclosure is not limited thereto.

After the methyltetrahydrophthalic anhydride product is manufactured, according to practical requirements, the properties of the methyltetrahydrophthalic anhydride product can be further adjusted through steps S4 to S6.

In step S4, the methyltetrahydrophthalic anhydride product (the hardener crude product) is delivered to an isomerization tank 2, so that the methyltetrahydrophthalic anhydride product and an alkaline catalyst C undergo the isomerization reaction at a temperature ranging from 130° C. to 160° C. Accordingly, an isomerization product (the low-viscosity hardener) is obtained. Specifically, step S4 is to perform the isomerization reaction on the 3-methyltetrahydrophthalic anhydride in the methyltetrahydrophthalic anhydride product. In this way, the cis-3-methyltetrahydrophthalic anhydride can be reconstituted into the trans-3-methyltetrahydrophthalic anhydride, so as to adjust the content ratio of the trans-3-methyltetrahydrophthalic anhydride to the cis-3-methyltetrahydrophthalic anhydride.

Before the isomerization reaction, the content of the trans-3-methyltetrahydrophthalic anhydride is lower than the content of the cis-3-methyltetrahydrophthalic anhydride in the methyltetrahydrophthalic anhydride product. After the isomerization reaction, the content of the trans-3-methyltetrahydrophthalic anhydride is greater than the content of the cis-3-methyltetrahydrophthalic anhydride in the isomerization product. The content ratio of the trans-3-methyltetrahydrophthalic anhydride to the cis-3-methyltetrahydrophthalic anhydride in the isomerization product (the low-viscosity hardener) can be monitored by the gas chromatograph. In one exemplary embodiment, the content ratio of the trans-3-methyltetrahydrophthalic anhydride to the cis-3-methyltetrahydrophthalic anhydride ranges from 1.1:1 to 4.8:1 (e.g., 1.5:1, 2:1, 2.5:1, 3:1, 3.5:1, 4:1, or 4.5:1).

In step S5, the isomerization product (the low-viscosity hardener) is introduced into a distillation column 3 for separation of the alkaline catalyst C and for a purification process. In step S6, the isomerization product (the low-viscosity hardener) is moved from the distillation column 3 to a preparation tank 4, and a stabilizer S (e.g., butylated hydroxytoluene (BHT)) can be optionally added to increase the shelf life of a product. However, the present disclosure is not limited thereto. In step S7, the product added with the stabilizer S is moved from the preparation tank 4 to a finished product storage tank 5 for product packaging.

With regard to how the methyltetrahydrophthalic anhydride is prepared in the present disclosure, Examples 5 to 7 below are exemplarily provided for convenience of description. Reaction parameters of Examples 5 to 7 are shown in Table 2.

Example 5

6,000 kilograms of the maleic anhydride is added into a reactor, and the reactor is heated to melt the maleic anhydride. When a temperature of the reactor reaches 70° C., the vaporized piperylene is introduced into the reactor for the first addition reaction. During the first addition reaction, the conversion rate of the maleic anhydride is monitored by the gas chromatograph. When the conversion rate of the maleic anhydride reaches 70% (which takes 12 hours), the introduction of the piperylene is stopped for completion of the first addition reaction.

The vaporized isoprene is introduced into the reactor for the second addition reaction. During the second addition reaction, the content of the maleic anhydride is monitored by the gas chromatograph. When the content of the maleic anhydride is less than 100 ppm (which takes 4 hours), the introduction of the isoprene is stopped for completion of the second addition reaction. After the residual gas in the reactor is discharged, the methyltetrahydrophthalic anhydride product (the hardener crude product) can be obtained.

In the methyltetrahydrophthalic anhydride product of Example 5, the weight ratio of the 3-methyltetrahydrophthalic anhydride to the 4-methyltetrahydrophthalic anhydride is 7:3, and the content ratio of the trans-3-methyltetrahydrophthalic anhydride to the cis-3-methyltetrahydrophthalic anhydride is 1:5.6.

Then, the methyltetrahydrophthalic anhydride product is delivered to the isomerization tank. After the sodium hydroxide (the alkaline catalyst) is added, the isomerization reaction proceeds at a temperature of 150° C. for 24 hours, so as to obtain the isomerization product (the low-viscosity hardener). Based on the detection made by the gas chromatograph, the content ratio of the trans-3-methyltetrahydrophthalic anhydride to the cis-3-methyltetrahydrophthalic anhydride in the isomerization product is 4.31:1, and the viscosity of the isomerization product is 33 cps. Afterwards, the final isomerization product can be obtained through the above-mentioned steps S5 to S7.

Example 6

6,000 kilograms of the maleic anhydride is added into the reactor, and the reactor is heated to melt the maleic anhydride. When the temperature of the reactor reaches 100° C., the vaporized piperylene is introduced into the reactor for the first addition reaction. During the first addition reaction, the conversion rate of the maleic anhydride is monitored by the gas chromatograph. When the conversion rate of the maleic anhydride reaches 50% (which takes 8.5 hours), the introduction of the piperylene is stopped for completion of the first addition reaction.

The vaporized isoprene is introduced into the reactor for the second addition reaction. During the second addition reaction, the content of the maleic anhydride is monitored by the gas chromatograph. When the content of the maleic anhydride is less than 100 ppm (which takes 6 hours), the introduction of the isoprene is stopped for completion of the second addition reaction. After the residual gas in the reactor is discharged, the methyltetrahydrophthalic anhydride product (the hardener crude product) can be obtained.

In the methyltetrahydrophthalic anhydride product of Example 6, the weight ratio of the 3-methyltetrahydrophthalic anhydride to the 4-methyltetrahydrophthalic anhydride is 1:1, and the content ratio of the trans-3-methyltetrahydrophthalic anhydride to the cis-3-methyltetrahydrophthalic anhydride is 1:5.2.

Then, the methyltetrahydrophthalic anhydride product is delivered to the isomerization tank. After the sodium hydroxide (the alkaline catalyst) is added, the isomerization reaction proceeds at a temperature of 150° C. for 20 hours, so as to obtain the isomerization product (the low-viscosity hardener). Based on the detection made by the gas chromatograph, the content ratio of the trans-3-methyltetrahydrophthalic anhydride to the cis-3-methyltetrahydrophthalic anhydride in the isomerization product is 3.5:1, and the viscosity of the isomerization product is 36 cps. Afterwards, the final isomerization product can be obtained through the above-mentioned steps S5 to S7.

Example 7

6,000 kilograms of the maleic anhydride is added into the reactor, and the reactor is heated to melt the maleic anhydride. When the temperature of the reactor reaches 100° C., the vaporized piperylene is introduced into the reactor for the first addition reaction. During the first addition reaction, the conversion rate of the maleic anhydride is monitored by the gas chromatograph. When the conversion rate of the maleic anhydride reaches 30% (which takes 4 hours), the introduction of the piperylene is stopped for completion of the first addition reaction.

The vaporized isoprene is introduced into the reactor for the second addition reaction. During the second addition reaction, the content of the maleic anhydride is monitored by the gas chromatograph. When the content of the maleic anhydride is less than 100 ppm (which takes 8 hours), the introduction of the isoprene is stopped for completion of the second addition reaction. After the residual gas in the reactor is discharged, the methyltetrahydrophthalic anhydride product (the hardener crude product) can be obtained.

In the methyltetrahydrophthalic anhydride product of Example 7, the weight ratio of the 3-methyltetrahydrophthalic anhydride to the 4-methyltetrahydrophthalic anhydride is 3:7, and the content ratio of the trans-3-methyltetrahydrophthalic anhydride to the cis-3-methyltetrahydrophthalic anhydride is 1:5.5.

The methyltetrahydrophthalic anhydride product is delivered to the isomerization tank. After the sodium hydroxide (the alkaline catalyst) is added, the isomerization reaction proceeds at a temperature of 150° C. for 16 hours, so as to obtain the isomerization product (the low-viscosity hardener). Based on the detection made by the gas chromatograph, the content ratio of the trans-3-methyltetrahydrophthalic anhydride to the cis-3-methyltetrahydrophthalic anhydride in the isomerization product is 4.1:1, and the viscosity of the isomerization product is 40 cps. Afterwards, the final isomerization product can be obtained through the above-mentioned steps S5 to S7.

TABLE 2

|  | Example 5 | Example 6 | Example 7 |
|---|---|---|---|
| Conversion rate of maleic anhydride (at an end of first addition reaction) | 70% | 50% | 30% |
| Reaction time of first addition reaction | 12 hours | 8.5 hours | 4 hours |
| Reaction time of second addition reaction | 4 hours | 6 hours | 8 hours |
| Weight ratio of 3-methyltetrahydrophthalic anhydride to 4-methyltetrahydrophthalic anhydride in methyltetrahydrophthalic anhydride product | 7:3 | 1:1 | 3:7 |
| Content ratio of trans-3-methyltetrahydrophthalic anhydride to cis-3-methyltetrahydrophthalic anhydride in methyltetrahydrophthalic anhydride product | 1:5.6 | 1:5.2 | 1:5.5 |
| Alkaline catalyst | Sodium hydroxide | Sodium hydroxide | Sodium hydroxide |
| Isomerization reaction temperature | 150° C. | 150° C. | 150° C. |
| Isomerization reaction time | 24 hours | 20 hours | 16 hours |
| Content ratio of trans-3-methyltetrahydrophthalic anhydride to cis-3-methyltetrahydrophthalic anhydride in isomerization product | 4.31:1 | 3.5:1 | 4.1:1 |
| Viscosity of isomerization product | 33 cps | 36 cps | 40 cps |

From the content of Examples 5 to 7, it can be observed that the content ratio of the 3-methyltetrahydrophthalic anhydride to the 4-methyltetrahydrophthalic anhydride in the methyltetrahydrophthalic anhydride product can be easily adjusted through the technical solution of adding the reactants in a stepwise manner as proposed in the present disclosure. Through this technical solution, the reaction efficiency of the reactants can be improved, such that the two addition reactions can be carried out at a low temperature. Furthermore, by adjusting the content ratio of the 3-methyltetrahydrophthalic anhydride to the 4-methyltetrahydrophthalic anhydride in the methyltetrahydrophthalic anhydride product, and adjusting the content ratio of the trans-3-methyltetrahydrophthalic anhydride to the cis-3-methyltetrahydrophthalic anhydride in the isomerization product, an effect of controlling a product viscosity can be achieved. Specifically, the viscosity of the isomerization product ranges from 32 cps to 42 cps.

Beneficial Effects of the Embodiments

In conclusion, in the method for manufacturing the low-viscosity hardener provided by the present disclosure, by virtue of "controlling contents of the 3-methyltetrahydrophthalic anhydride and the 4-methyltetrahydrophthalic anhydride in the hardener crude product" and "adding the alkaline catalyst for the isomerization reaction," the effect of reducing the viscosity of the hardener can be achieved. In this way, the low-viscosity hardener can have a wider applicability.

More specifically, in the present disclosure, the piperylene is added into the reactor for the first addition reaction, and the isoprene is added into the reactor for the second addition reaction. Such a technical solution allows the reaction efficiency for preparing the methyltetrahydrophthalic anhydride to be improved. Accordingly, in the present disclosure, the addition reactions can be carried out at a temperature ranging from 80° C. to 120° C., and the manufacturing costs can be reduced.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A method for manufacturing a low-viscosity hardener, comprising:

feeding maleic anhydride into a reactor;

adding piperylene into the reactor, so that the piperylene and the maleic anhydride undergo a first addition reaction;

adding isoprene into the reactor, so that the isoprene and the maleic anhydride undergo a second addition reaction to obtain a hardener crude product; wherein, when a conversion rate of the maleic anhydride is greater than 25%, the first addition reaction is complete and the isoprene is added into the reactor; wherein the hardener crude product contains 3-methyltetrahydrophthalic anhydride and 4-methyltetrahydrophthalic anhydride, and a weight ratio of the 3-methyltetrahydrophthalic anhydride to the 4-methyltetrahydrophthalic anhydride ranges from 7:3 to 3:7; and subjecting the hardener crude product and an alkaline catalyst to an isomerization reaction, so as to obtain the low-viscosity hardener; wherein a viscosity of the low-viscosity hardener ranges from 30 cps to 50 cps.

2. The method according to claim 1, wherein the isomerization reaction is carried out at a temperature ranging from 130° C. to 160° C.

3. The method according to claim 1, wherein the alkaline catalyst is selected from the group consisting of potassium carbonate, sodium carbonate, sodium hydroxide, potassium hydroxide, ethanolamine, diethanolamine, and triethanolamine.

4. The method according to claim 1, wherein t ratio of trans-3-methyltetrahydrophthalic anhydride to cis-3-methyltetrahydrophthalic anhydride in the low-viscosity hardener ranges from 1.1:1 to 4.8:1.

5. The method according to claim 1, wherein a content ratio of trans-3-methyltetrahydrophthalic anhydride to cis-3-methyltetrahydrophthalic anhydride in the hardener crude product ranges from 1:4 to 1:7.

6. The method according to claim 1, wherein the first addition reaction is carried out at a temperature ranging from 80° C. to 120° C., and the second addition reaction is carried out at a temperature ranging from 80° C. to 120° C.

7. The method according to claim 1, wherein, when a content of the maleic anhydride is less than 100 ppm, the second addition reaction is complete.

8. The method according to claim 1, wherein a purity of the piperylene ranges from 65% to 75%, and a purity of the isoprene is greater than 99%.

* * * * *